(12) United States Patent
Breen et al.

(10) Patent No.: US 11,291,380 B2
(45) Date of Patent: Apr. 5, 2022

(54) BLOOD VOLUME MONITOR

(71) Applicant: University of Western Sydney, Penrith (AU)

(72) Inventors: Paul Breen, Redfern (AU); Gaetano Gargiulo, Kogarah (AU)

(73) Assignee: Western Sydney University

( * ) Notice: Subject to any disclaimer, the term of this patent is extended or adjusted under 35 U.S.C. 154(b) by 611 days.

(21) Appl. No.: 15/100,243

(22) PCT Filed: Nov. 27, 2014

(86) PCT No.: PCT/AU2014/050379
§ 371 (c)(1),
(2) Date: May 27, 2016

(87) PCT Pub. No.: WO2015/077838
PCT Pub. Date: Jun. 4, 2015

(65) Prior Publication Data
US 2017/0000360 A1    Jan. 5, 2017

(30) Foreign Application Priority Data
Nov. 28, 2013    (AU) ................................ 2013904603

(51) Int. Cl.
*A61B 5/0295*    (2006.01)
*A61B 5/00*    (2006.01)
(Continued)

(52) U.S. Cl.
CPC .......... *A61B 5/0295* (2013.01); *A61B 5/0531* (2013.01); *A61B 5/0535* (2013.01);
(Continued)

(58) Field of Classification Search
None
See application file for complete search history.

(56) References Cited

U.S. PATENT DOCUMENTS 3,835,840 A     9/1974  Mount
4,258,720 A *   3/1981  Flowers ............... A61B 5/1073
                                                     600/500
(Continued)

FOREIGN PATENT DOCUMENTS

JP    S63-281626 A    11/1988
JP    2002-514113 A    5/2002
(Continued)

OTHER PUBLICATIONS

Barbara M. Doucet, Neuromuscular Electrical Stimulation for Skeletal Muscle Function, 2012, Yale Journal of Biology and Medicine, 85, pp. 201-215.*
(Continued)

*Primary Examiner* — Alex M Valvis
*Assistant Examiner* — Chanel J Jhin
(74) *Attorney, Agent, or Firm* — TraskBritt

(57) ABSTRACT

A blood volume monitor includes a carrier mountable on a subject's body part. A measuring arrangement is mounted on the carrier. The measuring arrangement provides data relating to a change in volume of the body part, and outputs signals representative of the change. A control unit is in communication with the measuring arrangement to process data output by the measuring arrangement to determine, using the volume data, the volume of the body part and determines blood volume in the body part. The control unit uses the response signals received from the measuring arrangement and the determined volume of the part of the body to determine the blood volume.

25 Claims, 10 Drawing Sheets

(51) Int. Cl.
*A61N 1/04* (2006.01)
*A61N 1/36* (2006.01)
*A61B 5/0531* (2021.01)
*A61B 5/11* (2006.01)
*A61B 5/0535* (2021.01)
*A61B 5/107* (2006.01)

(52) U.S. Cl.
CPC .............. *A61B 5/1073* (2013.01); *A61B 5/11* (2013.01); *A61B 5/6828* (2013.01); *A61N 1/0452* (2013.01); *A61N 1/36003* (2013.01); *A61B 5/1116* (2013.01); *A61B 5/6831* (2013.01); *A61B 2562/043* (2013.01)

(56) References Cited

U.S. PATENT DOCUMENTS

| | | | | |
|---|---|---|---|---|
| 4,875,488 | A * | 10/1989 | Shimazu | A61B 5/1073 600/507 |
| 6,015,393 | A | 1/2000 | Hovland et al. | |
| 6,301,500 | B1 * | 10/2001 | Van Herk | A61B 5/0531 600/393 |
| 8,162,857 | B2 | 4/2012 | Lanfermann et al. | |
| 2006/0094964 | A1 | 5/2006 | Ragauskas et al. | |
| 2006/0247538 | A1 * | 11/2006 | Davis | A61B 5/02007 600/481 |
| 2008/0077024 | A1 | 3/2008 | Schnall | |
| 2009/0177099 | A1 | 7/2009 | Smith et al. | |
| 2009/0287102 | A1 | 11/2009 | Ward | |
| 2010/0094140 | A1 | 4/2010 | Pranevicius et al. | |
| 2010/0179421 | A1 | 7/2010 | Tupin | |
| 2012/0095355 | A1 | 4/2012 | Zdeblick | |
| 2015/0359644 | A1 * | 12/2015 | Sanders | A61F 2/7812 623/34 |

FOREIGN PATENT DOCUMENTS

| | | |
|---|---|---|
| JP | 2012-520157 A | 9/2010 |
| WO | WO 98/42255 A1 | 10/1998 |
| WO | WO 2008/004159 A2 | 1/2008 |
| WO | WO 2010/105250 A2 | 9/2010 |
| WO | WO 2013069002 A1 * | 5/2013 ........... A61B 5/6828 |

OTHER PUBLICATIONS

Scott D. Bennie, Toward the optimal waveform for electrical stimulation of human muscle, Apr. 22, 2002, Eur J Appl Physiol, 88, pp. 13-19.*

Gad Alon, Effects of Electrode Size on Basic Excitatory Responses and on Selected Stimulus, Jul. 1994, JOSPT, vol. 20 No. 1, pp. 29-35.*

Supplemental European Search Report in corresponding European Application No. EP 14 86 6613, dated May 26, 2017.

Office Action in related Japanese Application No. 2016-533530, dated Jul. 3, 2018.

Notice for Reasons for Rejection in corresponding Japanese Patent Application No. 2016-533530, dated Jan. 8, 2019.

* cited by examiner

BLOOD VOLUME MONITOR

CROSS-REFERENCE TO RELATED APPLICATIONS

This application is a national phase application under 35 U.S.C. § 371 of International Application No. PCT/AU2014/050379, filed on Nov. 27, 2014, which claims the benefit of Australian Provisional Patent Application No 2013904603 filed on 28 Nov. 2013, the contents of which are incorporated herein by reference in their entirety.

TECHNICAL FIELD

This disclosure relates, generally, to monitoring blood volume in a subject and, more particularly, to a blood volume monitor and to a method of monitoring blood volume.

BACKGROUND

Non-invasive monitoring of blood volume is normally achieved using a 4-point body impedance measurement system known as electrical impedance plethysmography (EIP). This measurement is common practice and is achieved by recording small voltage drops across a pair of electrodes responsive to a high frequency (>10 kHz) sinusoidal constant current stimulus applied via a separate pair of electrodes.

EIP requires that all four electrodes are placed in a specific geometric configuration and the skin is carefully prepared. Skin preparation usually includes shaving of hair and skin abrasion to achieve electrode contact impedance below 5 k$\Omega$ with less than 20% impedance imbalance between electrodes. The recorded voltages then are divided by the current amplitude to estimate the blood impedance, the higher the impedance (higher voltage) the smaller is the volume of blood in the measured region. Although non-invasive, the procedure is cumbersome. Furthermore, no system currently available is capable of long term monitoring as changes in electrode impedance (due to degradation over time) will affect the recording.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In a first aspect, there is provided a blood volume monitor which includes a carrier mountable about a part of a body of a subject;

a measuring arrangement mounted on the carrier, the measuring arrangement comprising at least one element configured to provide volume data relating to a volume of the part of the body of the subject underlying the carrier and for measuring change in volume of the part of the body of the subject underlying the carrier and for outputting response signals representative of the change in volume; and a control unit in communication with the measuring arrangement to process data output by the measuring arrangement to determine, using the volume data, the volume of the part of the body of the subject underlying the carrier and to determine blood volume in the part of the body of the subject, the control unit using the response signals received from the measuring arrangement and the determined volume of the part of the body to determine the blood volume.

It is an advantage of the disclosure that the blood volume monitor outputs data relating to blood volume in units of volumetric measurement, such as, for example, in millilitres.

The response signals may represent a blood impedance value of blood in the part of the body of the subject.

The carrier may be in the form of a sleeve of a resiliently flexible material.

In an embodiment, the measuring arrangement may include a sensing arrangement comprising a plurality of sets of impedance measuring elements for measuring changes in impedance in the part of the body of the subject, such changes in impedance being indicative of blood volume changes, and, hence, change in volume, in the part of the body of the subject, one set of the elements operating at any one time as stimulating elements for stimulating the part of the body of the subject with at least one of the other sets of elements sensing response signals evoked in the part of the body of the subject.

Each element of the sets of elements may be an electrode, the electrodes being arranged at circumferentially spaced intervals about the sleeve and each set of electrodes comprising a pair of opposed electrodes. One of the pairs of electrodes may be configured to be used at any one time as stimulating electrodes and at least one other pair of electrodes, rotated about the carrier relative to the one pair of electrodes, is used as sensing electrodes. The control unit may be operable to cycle through the pairs of electrodes periodically to vary which pair of electrodes is operating as the stimulating electrodes and which pair of electrodes is being used as sensing electrodes.

The control unit may be operable to cycle through the sets of electrodes to select the stimulating set of electrodes prior to the stimulating set of electrodes stimulating underlying tissue of the subject.

A stimulating signal output by the stimulating set of elements is one of a sine wave signal and it uniform pulse waveform. By "uniform" is meant that the pulse of one polarity has the same amplitude and duration as the pulse of the opposite polarity.

The amplitude of the stimulating signal is selected to be lower than a level at which the subject is aware of the stimulation. In other words, the stimulating signal has a sub-sensation amplitude.

The control unit may be operable to vary an amplitude of the stimulating signal to account for changes in at least one of contact impedance and muscle contraction/relaxation.

The monitor may be configured to impart muscular stimulation to muscles of the subject. Hence, the monitor can also be used to effect muscular stimulation in non-active subjects, either because of injury, infirmness or due to being under anaesthesia. The monitor may use any electrodes of the sensing/stimulating arrangement to effect muscular stimulation. Instead, the monitor may include dedicated muscular stimulation electrodes.

The measuring arrangement may further include a volume determining mechanism, comprising at least one volume measuring element, carried by the sleeve, at least a part of the volume determining mechanism being configured to expand and contract in unison with the sleeve.

The volume determining mechanism may comprise at least one element configured to approximate a truncated cone. Thus, for example, the volume determining mechanism may comprise a pair of annular, resiliently flexible bands arranged in spaced relationship, the bands being interconnected by a height approximating member for approximating the height of the truncated cone. Other configurations of the volume determining mechanism may include at least one helically wound member carried by the sleeve or a plurality of abutting annular elements.

In another embodiment, the measuring arrangement may be configured so that the same sets of elements provide both the volume data and measure the change in volume of the part of the body of the subject underlying the carrier to output the response signals representative of the change in volume.

The monitor may include a position detecting mechanism for detecting a position of the part of the body of the subject.

The monitor may include a pressure imparting mechanism for imparting pressure to the part of the body of the subject.

According to a second aspect of the disclosure, there is provided a method of monitoring blood volume, the method including
determining the volume of a part of a body of a subject;
sensing change in volume of the part of the body; and
determining the volume of blood in the part of the body based on the determined volume and the sensed change in volume of the part of the body.

The method may include sensing change in volume in the part of the body of the subject by sensing change in impedance of blood within the part of the body of the subject.

In an embodiment, the method may include sensing the change in impedance by stimulating the part of the body with a first set of sensing elements and monitoring an evoked response with at least one further set of sensing elements.

The method may include cycling through the sets of elements to vary which set of elements is functioning as the set of stimulating elements at any one time.

The method may includes effecting stimulation with one of a sine wave signal and a uniform pulse waveform. The method may include selecting the amplitude of the stimulating signal to be lower than a level at which the subject is aware of the stimulation. The method may include varying an amplitude of the stimulating signal to account for changes in contact impedance or muscle contraction/relaxation.

The method may include determining the volume of the part of the body of the subject by using a volume determining mechanism carried on a carrier configured to be placed over the part of the body of the subject. The volume determining mechanism may comprise at least one element configured to approximate a truncated cone and the method may include determining the volume of the truncated cone.

In an embodiment, the method may include using the volume determining mechanism also to sense the change in volume of the part of the body of the subject underlying the carrier.

The method may include imparting muscular stimulation to muscles of the subject.

The method may include detecting a position of the part of the body of the subject.

The method may include imparting pressure to the part of the body of the subject.

BRIEF DESCRIPTION OF DRAWINGS

Embodiments of the disclosure are now described by way of example with reference to the accompanying drawings, in which.

DETAILED DESCRIPTION OF EXEMPLARY EMBODIMENTS

Figure 1:
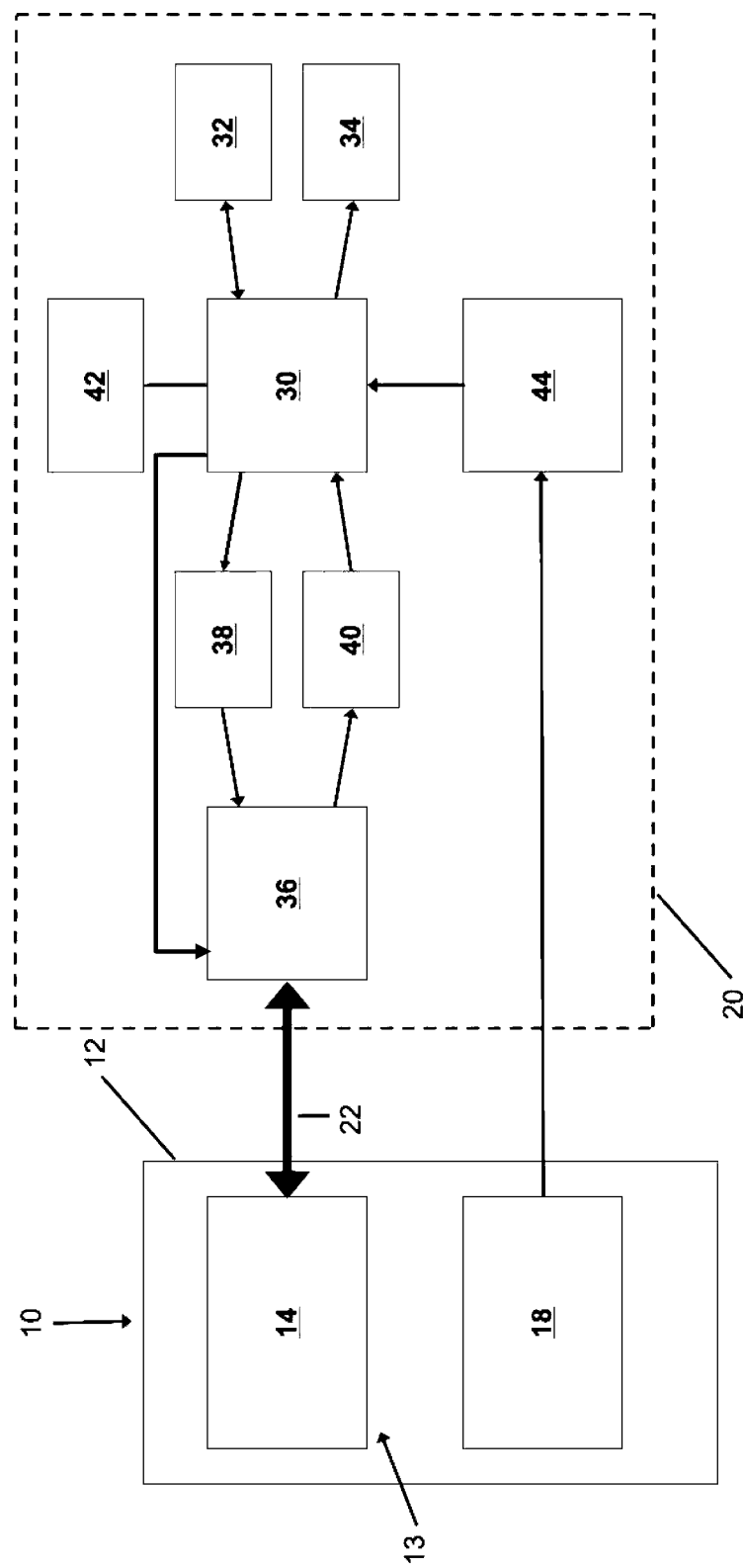
FIG. 1 shows a schematic block diagram of an embodiment of a blood volume monitor.

In FIGS. 1-12 of the drawings, reference numeral 10 generally designates an embodiment of a blood volume monitor. The monitor 10 includes a carrier 12 mountable about a part of a body of a subject as will be described in greater detail below. The monitor 10 includes a measuring arrangement 13 carried by the carrier 12. In this embodiment of the disclosure, the measuring arrangement 13 comprises a sensing arrangement 14 mounted on the carrier 12 and a volume determining mechanism 18 associated with the carrier for determining a volume of the part of the body of the subject underlying the carrier 12.

Figure 5:
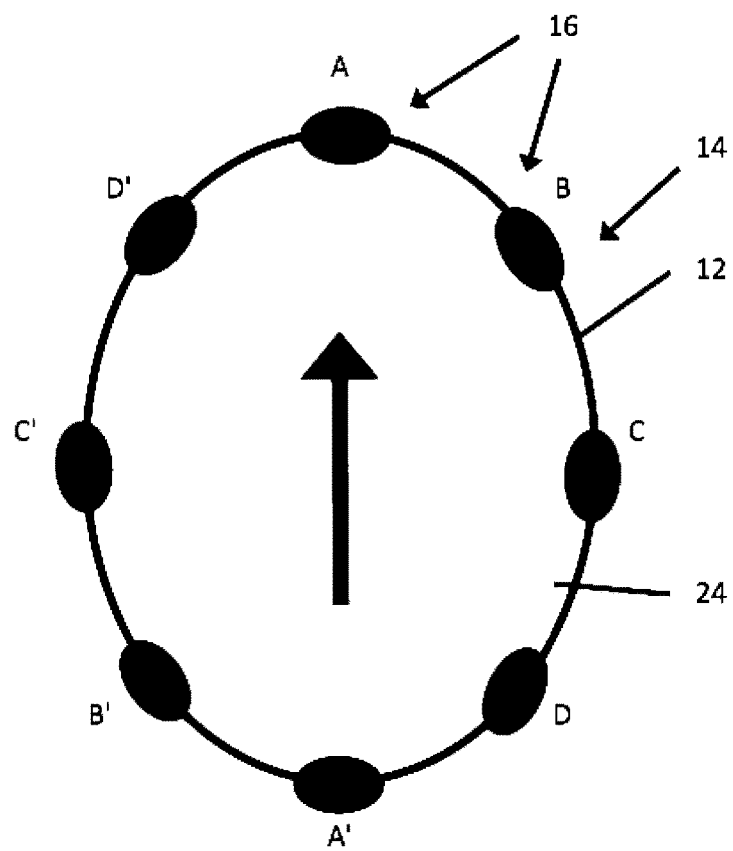
FIG. 5 shows a schematic representation of a sensing arrangement of the blood volume monitor of FIG. 1.

As illustrated, more clearly in FIG. 5 of the drawings, the sensing arrangement 14 comprises a plurality of sets of elements or electrodes 16. The electrodes 16 are arranged in pairs with electrodes 16 of each pair being arranged in opposed relationship, as shown in FIG. 5 by the labels A-A', B-B', C-C' and D-D'.

The monitor 10 includes a control unit 20 which is in communication with the carrier 12 and, in particular, the components 14 and 18 carried on the carrier 12, as indicated by the arrows 22. As will be described in greater detail below, the control unit 20 is operable initially to select one of the pairs of electrodes 16 as a stimulating pair of electrodes with the remaining pairs of electrodes sensing response signals arising as a result of stimulation of the part of the subject's body by the set of stimulating electrodes 16. The control unit 20 is further operable to cycle through the pairs of electrodes 16 to vary which pair of electrodes is operable as the set of stimulating electrodes 16 with at least one of the non-selected, remaining pairs of electrodes 16 sensing the response signals.

Figure 2:
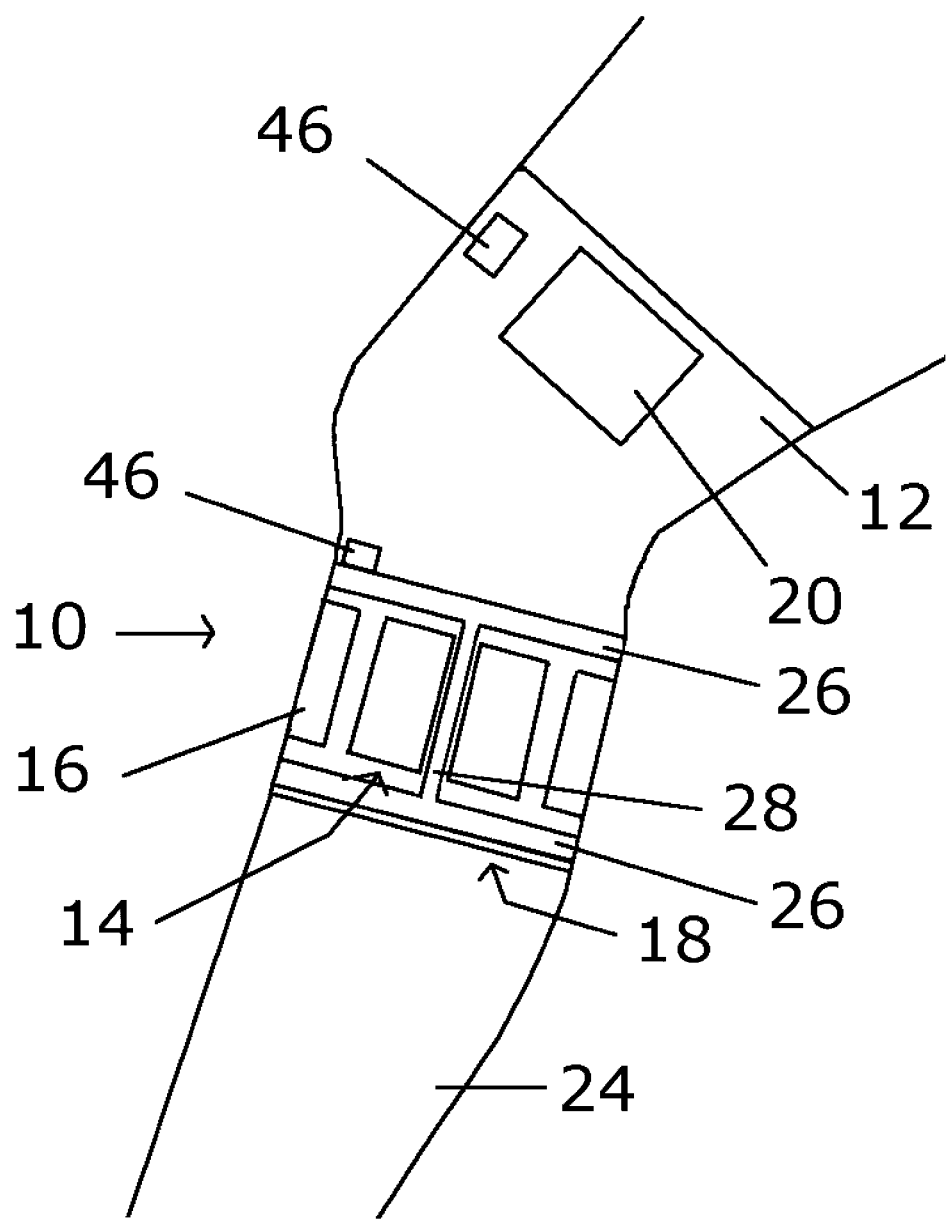
FIG. 2 shows a schematic representation of a use of the blood volume monitor of FIG. 1.
Figure 3:
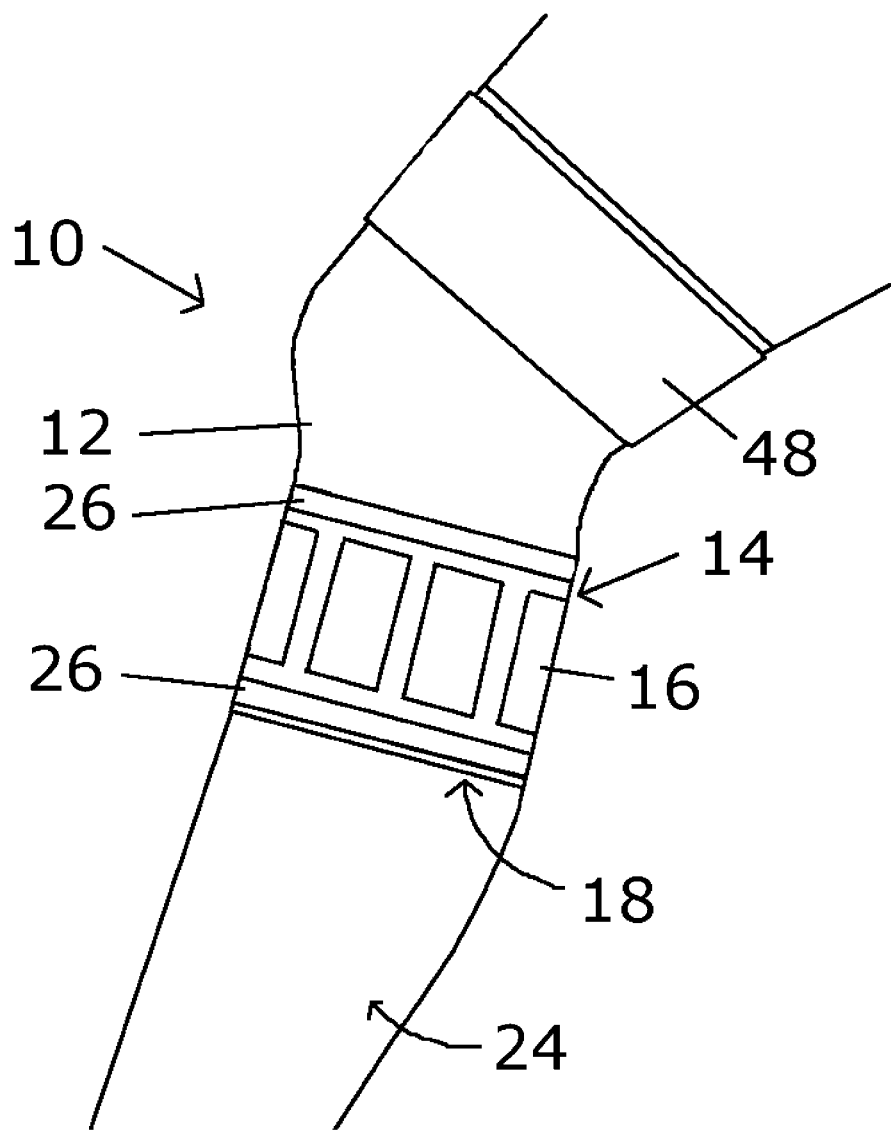
FIG. 3 shows a schematic representation of another use of the blood volume monitor of FIG. 1.
Figure 4:
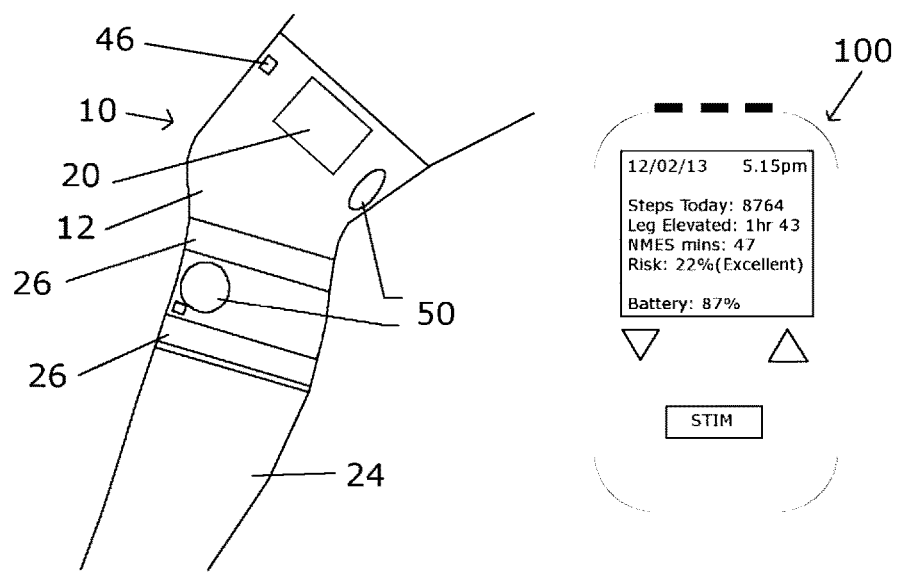
FIG. 4 shows a schematic representation of a further use of the blood volume monitor of FIG. 1.

The monitor 10 is intended particularly for use in electrical impedance plethysmography (EIP) applications and is intended for mounting about a limb of a subject's body, in particular, a lower part of the limb, as shown by the lower part of the leg 24 of the subject in FIGS. 2-4 of the drawings. The monitor 10 could also be used for EIP measurements of a subject's neck vasculature by being placed about a subject's neck. In addition, the monitor 10 could also be placed about a subject's chest and be used to measure volume. By measuring volume variation due to heartbeat, the monitor 10 could be used to determine the volume displaced by the heartbeat and from measurement of blood impedance could determine how much of the volume variation is due to blood flow. In so doing, the monitor 10 could be used to monitor cardiac output of a subject's heart. In the remainder of this specification, the monitor 10 will be described with reference to use on a subject's leg 24.

The carrier 12 is in the form of a sleeve of a resiliently flexible material on which the electrodes 16 are mounted. The control unit 20 is, as shown in FIG. 2 of the drawings, also mounted on the sleeve 12 although this is not necessarily applicable in all embodiments. In some embodiments, the control unit 20 may be mounted remotely from the sleeve 12 and communicate, either via a wired or wireless communications link, with the components 14 and 18 on the sleeve 12.

As described above, the sensing arrangement 14 comprises a plurality of sets of electrodes 16 arranged in opposed pairs about the circumference of the sleeve 12.

The volume determining mechanism 18 can adopt various forms. In the illustrated embodiment of FIG. 2 of the drawings, the volume determining mechanism comprises a pair of spaced bands 26 of an electrically resistive material arranged circumferentially about the sleeve 12. The bands 26 are interconnected via a further, longitudinal extending strip 28 which is also of an electrically resistive material. The hands 26 and the strip 28 are resiliently flexible and their resistivity increases with increasing extension.

The bands 26 and the strip 28, when the sleeve 12 is placed about the leg 24 of the subject, measure the volume of that part of the leg circumscribed by the bands 26. The relevant part of the leg approximates a truncated cone and the bands 26 are used to measure that volume using the following equation:

$$V = (\frac{\pi}{3})(h)(b^2 + ab + a^2)$$

where a and b are the radii of each of the bands 26, and h is the height of the truncated cone.

The height of the truncated cone, h, can be estimated as follows: If the sleeve 12 has a fixed (known) and non-stretchable (or negligibly stretchable) length dimension "k" (being the spacing between the bands 26), then h=k*sin(abs (b−a)). If the sleeve 12 is resiliently flexible, i.e. has a non-negligible stretchability along its dimension "k", $k_{av}$ is measured as the average of measurement taken from a number (N) of stretch sensors placed vertically alongside the sleeve and is calculated as $k_{av}=(k_1+k_2+ \ldots +k_n)/N$ and:

$$h=k_{av}*\sin(abs(b-a)).$$

It will be appreciated that the sleeve 12 may be designed to have limited or almost no stretch in the direction of the strip 28. In such an embodiment, the strip 28 can be omitted with the spacing between the bands 26 being known and approximating the height of the truncated cone.

To enable the volume measurement to be made, the volume determining mechanism 18 is calibrated against known cylinders and known cones to ensure volume estimation within a tolerance of approximately 10% of specific calibration values, can be written as parameters inside the control unit 20 and used to perform precise measurements. At least two known values of known cylinders and known cones are required to make a linear approximation and to effect calibration.

In another embodiment, instead of the bands 26 and strip 28, the volume determining mechanism 18 comprises a single, helically coiled sensor 102 (FIG. 10) arranged within or on the sleeve 12. This allows a more direct estimation of volume as the targeted limb for the monitor 10, such as the subject's leg 24, can assume various shapes and the shape itself may change depending on movement and/or position of the limb. Once again, the helically coiled sensor 102 is of a resiliently flexible, electrically resistive material, the resistance of which increases with extension.

The helically coiled sensor 102 is calibrated against known volumes, again using known cones or cylinders. Once again, at least two values are required for a linear approximation and the first value should be determined using a cylinder with dimensions over which the sleeve 12 is a snug fit with no sagging or excessive stretching.

As with the first embodiment, calibration could be used to ensure error is within the prescribed tolerance or can be recorded in the software of the control unit 20 as a parameter to enable precise calculations of volume to be effected.

In yet a further embodiment, the volume determining mechanism 18 comprises a plurality of hands 104 (FIG. 11) which are stacked together, each band 104 approximating the volume of a truncated cone with the sum of the truncated cones approximating the volume of the part of the limb under the sleeve 12. Each hand 104 is of a resiliently flexible, electrically resistive material, the resistance of which increases with extension.

In this embodiment, calibration is effected as per the first embodiment above.

Referring again to FIG. 1 of the drawings, the control unit 20 includes a central processing unit, or processor, 30 which controls transmission of stimulating signals to the pair of electrodes 16 of the sensing arrangement 14 selected at any one time to be the stimulating electrodes and processes response signals received from those electrodes 16 acting as sensing electrodes.

The processor 30 incorporates a user interface 36 which allows a user to input data in a data storage module 32 of the control unit 20. The data storage module 32 also includes calibration data for the volume determining mechanism 18 as described above. The processor 30 supervises all activities of the control unit 20 and, for example, is used for sampling, acquiring and storing data in a digital format, doing any analogue to digital conversion where required, etc. The processor 30 further runs software to enable a user to perform calculations on received data, effectively in real time, these data including impedance measurements, volume calculations and generation of any alarm signals. The software also provides connectivity for the control unit 20 via a communications module 34.

As described above, the monitor 10 cycles through the pairs of electrodes 16 to vary which pair, at any one time, is functioning as the pair of stimulating electrodes and which of the remaining pairs of electrodes 16, or all of the remaining pairs, are used as sensing electrodes for monitoring response signals. The control unit 20 includes an interface 36 to control switching of the electrodes 16. The interface 36 includes a multiplexer for switching between the pairs of electrodes 16 to be used as the stimulating electrodes at any particular time.

The control unit 20 further includes a stimulator module 38 in communication with the interface 36. Data from the stimulator module 38 are fed via the interface 36 to the sensing arrangement 14. The stimulator module 38 makes use either of sine wave current stimulation or, in a preferred embodiment, a pulse waveform current stimulation where the pulses of the pulse waveform are uniform pulses (as defined). The sine waveform or the pulse waveform, as the case may be, is of controlled amplitude and period. The stimulating signal from the stimulator module 38 is fed to the interface 36 and from there to the sensing arrangement 14. As described, the multiplexer of the interface 36 cycles through the pairs of electrodes to periodically vary which pair of electrodes is being used for stimulating with the remaining pairs of electrodes 16 being used as sensing electrodes. The multiplexer 36 switches the stimulating electrodes 16 prior to the stimulating waveform output by the stimulator module 38.

Response signals received from the sensing electrodes 16 of the sensing arrangement 14 are fed via the interface 36 to a signal conditioning module 40. The signal conditioning module 40 is operable to provide amplification and filtering of the response signals. It is to be noted that the electrodes 16 are applied to the skin of the subject without any preparation having been made to the skin of the subject. In particular, no contact gels or preparation of the subject's skin by shaving or abrading is required. The electrodes 16 which are used are dry electrodes of a conductive, elastomeric material. As a result, the amplification circuitry 40 needs to have a high input impedance. Filtering also needs to take place to remove artefacts such as noise artefacts.

In addition, the signal conditioning module 40 is of sufficient sensitivity to enable the monitor 10 to be used in electromyography (EMG) applications to detect muscular activity in the region of the monitor 10 on the subject.

The control unit 20 is battery operated and includes a battery pack 42. The battery pack 42 is a rechargeable battery pack which is configured not to operate when a charging cord is connected unless the charger is a medical device approved charger. Such a charger requires galvanic isolation.

The battery pack 42 makes use of one or more lithium-ion rechargeable batteries and having a proprietary non-standard connector. The battery or batteries must be removed for recharging.

The data storage module 32 has two components, being an on-board removable memory on which is stored the software, factory calibration data, etc. The data stored in the on-board memory are able to be updated by a dedicated connection.

The second component of the data storage module 32 comprises a user-accessible memory, such as, for example, a memory card. The memory card stores event data, alarms, compressed measuring data, user calibration data, time stamps, or the like.

The communications module 34 includes a dedicated, isolated USB connector, wireless communications connectivity and mobile telephone connectivity such as GSM connectivity.

The control unit 20 includes a further signal conditioning module 44 for conditioning signals received from the volume determining mechanism 18. The signal conditioning module 44 conducts buffering, amplification and filtering operations to condition signals received from the volume determining mechanism prior to being fed to the processor 30 of the control unit 20.

As shown more clearly in FIG. 2 of the drawings, the monitor 10 also includes a position detecting mechanism in the form of at least two accelerometers 46. The accelerometers 46 are triaxial accelerometer devices and their placement on the sleeve 12 will vary according to which limb of the subject is being monitored. As an example, and as shown in FIG. 2 of the drawings, one of the accelerometers 46 is placed on the sleeve 12 below the knee to monitor position, i.e. torsional activity, of the lower limb 24 for artefacts detection. The second accelerometer 46 is placed above the knee of the subject to distinguish between positions and postures which do not vary the position of the monitor 10 significantly in the gravity field. For example, when the subject is sitting with the foot resting flat on the floor and when the subject is standing, the position of the monitor 10 in the gravity field will be substantially the same but blood flow considerations may vary.

In another application of the monitor 10, the monitor 10 includes a pressure imparting mechanism in the form of a pressure cuff 48 (FIG. 3). This application of the monitor 10 is in the detection of deep vein thrombosis (DVT) and will be described in greater detail below.

Still a further application of the monitor 10 is for effecting neuromuscular electrical stimulation. In this embodiment, as shown in FIG. 4 of the drawings, the monitor 10 includes neuromuscular electrical stimulation electrodes 50 as will be described in greater detail below. It will be appreciated that at least those neuromuscular electrical stimulation electrodes 50 configured to be placed below the knee of the subject could be implemented by the electrodes 16 of the sensing arrangement 14 of the monitor 10 on the sleeve 12.

With reference to FIG. 2 of the drawings, the monitor 10 is intended to measure the volume of blood (in millilitres) present at any given location of a subject's limb such as the lower leg 24 where the portion of the limb is of known volume or measurable volume (in litres). As will be appreciated, blood is highly conductive and its impedance is linked to both its viscosity and its oxygenation.

The control unit 20 energises one of the sets of electrodes 16 using a sine wave or pulse waveform to cause the electrodes 16 of the set to generate a stimulating signal which is input into the part of the subject's body underlying the carrier 12. A response signal evoked by the stimulating signal is sensed by at least one other sets of electrodes, rotationally spaced on the carrier 16 relative to that set of electrodes used as the stimulating electrodes. In an embodiment, the sensing set of electrodes 16 may be orthogonally arranged relative to the stimulating set of electrodes 16.

Further, in an embodiment, the control unit 20 is configured to cycle through the sets of electrodes 16 to vary the selection of the sets of electrodes to be used for stimulating and to be used for sensing, respectively.

Also, the monitor 10 is intended to enable long term recording of blood volume to be effected while the monitor 10 is worn by the subject. To cater for movement, the control unit 20 is operable to discard movement data artefacts as measured by the accelerometers 46. As the monitoring of blood volume during excessive movement is not efficient, any data having an average acceleration as averaged across all of the accelerometers 46 of greater than 1.1 g is discarded. As the subject may also be moving in the gravity field, for example, driving or sitting in a moving vehicle, the control unit 20 makes use of the first derivative of acceleration. In so doing, data relating to abrupt acceleration gradients can be discarded.

Still further, as indicated above, the processes 30 of the control unit has a user interface. The subject is able to flag to the monitor 10 if a particular posture is to be kept for longer than usual, for example, when sitting in a vehicle or retiring for the night. The control unit 20 is operable to vary the data collection regime to take into account such activities by the subject.

Although EIP is able to be performed using sine waves, the stimulator module 38 of the control will 20 of the monitor 10 is in a preferred application, operative to generate a pulse waveform. The pulse waveform is configured to be suitable for painless muscle stimulation using a biphasing fast rise charge-balanced pulse. For EIP purposes, the amplitude of the pulse is kept at a sub-stimulation threshold so that it will not be felt by the subject. The control unit 20 is operable to monitor changes in contact impedance and muscle contraction and relaxation of the subject. In this way, the control unit 20 is configured to change the amplitude of the pulses to cater for changes in operating conditions such as changes in the contact impedance and muscle contraction/relaxation.

The delivered amount of charge, as governed by the pulse width, can be changed to meet the required stimulating demand. In EIP applications, the pulses have a length of approximately 125 µS. This reduces the analogue sampling rate and, as a result, decreases computational effort required to analyse the sensed data.

Gross regulation of the amplitude and pulse width of the pulse waveform is able to be effected by the practitioner and the subject via the user interface of the processor 30 of the control unit 20. The user interface of the processor 30 is a two-level interface so that the subject has limited setting privileges while the practitioner has administrative privileges as well.

Fine regulation of the pulse amplitude and width is also automated and is based upon the RMS value of the detected surface EMG amplitude. For a freshly installed device, using tentative values regulated by the practitioner, EMG signals are measured at a spaced pair of electrodes to the stimulating pair of electrodes by varying the stimulation parameter in an attempt to minimise the recorded muscle activity. The measurement step is repeated for all possible combinations of pairs of stimulation/sensing electrodes while recording the corrected values for each stimulation pair which are then stored in the data storage module 32 of the control unit 20. The equivalent delivered charge and stimuli current are then calculated (according to the circuit parameters and the well know relationship I=dp/dt) and stored in the data storage module 32.

The frequency of the stimulation pulses can be dynamically changed to meet stimulation requirements. However, as 6 Hz is the normal low-pass cut off frequency for EIP devices and as the monitor 10 uses a pulse waveform, the stimulation frequency should be not lower than 12 Hz so as not to violate the Nyquist sampling requirement.

Blood impedance is measured in one of two ways, either by software methods or by hardware methods. The basic assumption is that the voltage measured from the measuring electrode pair divided by the equivalent stimulation current contains information about impedance gradients of tissue underlying the electrodes 16. In addition, because the waveform is a pulse waveform, it is possible to assume that the slow changing impedance modulates the recorded pulse waveform. Because of the fast rise of the stimulating pulse, the effective real value of the impedance is reached at the maximum value of the recorded pulses. Any capacitance charge/discharge effects at the rise and fall edges of the pulse can be ascribed to skin and other tissue capacitances which do not need to be taken into account for blood volume measurements.

Insofar as the software methods are concerned, some of the different ways in which impedance can be determined are as follows:

(a) measurement of the maximum value in the stimuli windows, (b) signal envelope extraction using full wave rectification plus low pass filtering, or (c) using an absolute value of the signal using a Hilbert's transform plus associated low pass filtering.

Regardless of the method employed, pre-processing of the response signals to remove power line noise artefacts and other high frequency noise artefacts is carried out using the signal conditioning module 40 prior to the processor 30 determining impedance.

Figure 6:
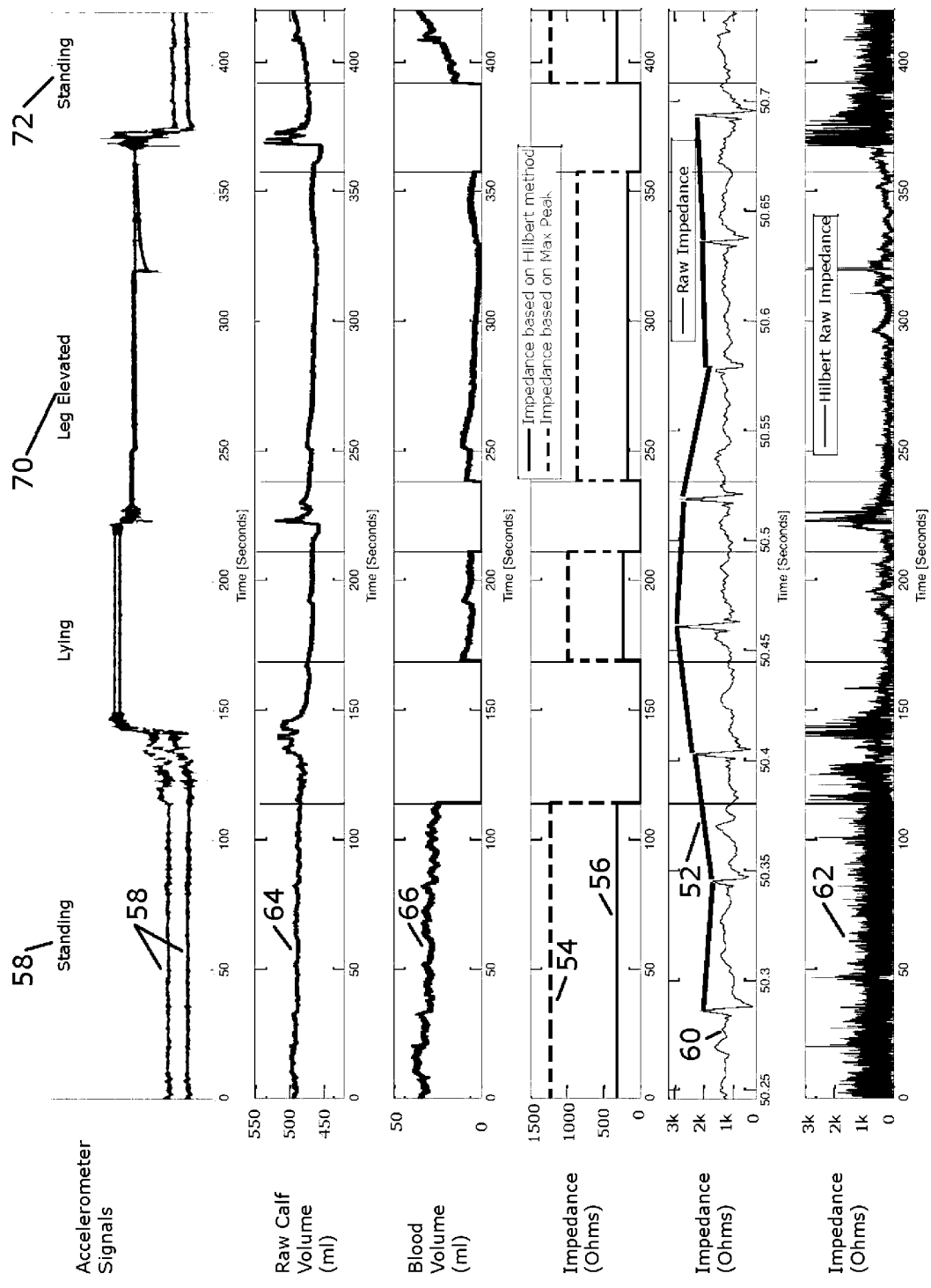
FIG. 6 shows a graphical representation of outputs of sensors of the monitor and processed output signals from the monitor.
Figure 7:
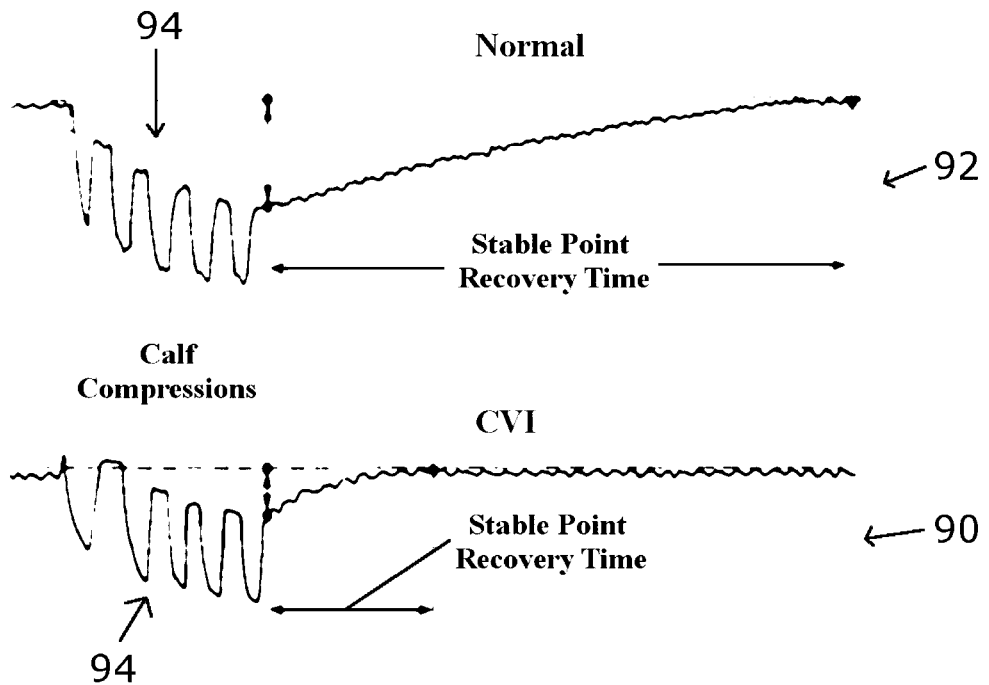
FIG. 7 shows a graphical representation of the use of the monitor shown in FIG. 2 of the drawings for measuring chronic venous insufficiency.
Figure 8:
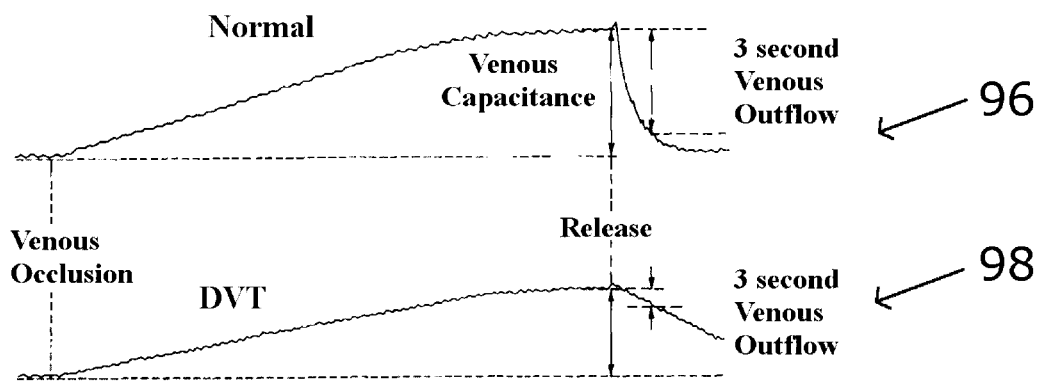
FIG. 8 shows a graphical representation of the use of monitor shown in FIG. 3 of the drawings for investigating the presence of deep vein thrombosis.

The first method of measuring impedance using the software measurements i.e. measurement of maximum value is shown by trace 52 in FIG. 6 of the drawings. Measuring that impedance based on maximum peak methods using the signal envelope extraction is shown by trace 54 in FIG. 6 of the drawings and measuring impedance using the Hilbert's transform is shown by trace 56 in FIG. 6 of the drawings.

The traces 58 at the top of FIG. 6 are signals representative of data output by the accelerometers 46 of the monitor 10, the upper trace being from the accelerometer 46 on the shank of the subject and the lower trace being from the accelerometer 46 on the thigh of the subject.

Raw impedance change data are shown by trace 60 and the Hilbert raw impedance change data are shown by trace 62 in FIG. 6 of the drawings. Trace 64 represents the raw volume data as measured by the volume determining mechanism 18 of the monitor 10 and trace 66 is the blood volume changes over time depending on the position of the subject as indicated by legends 68, 70 and 72 in FIG. 6 of the drawings.

Figure 9:
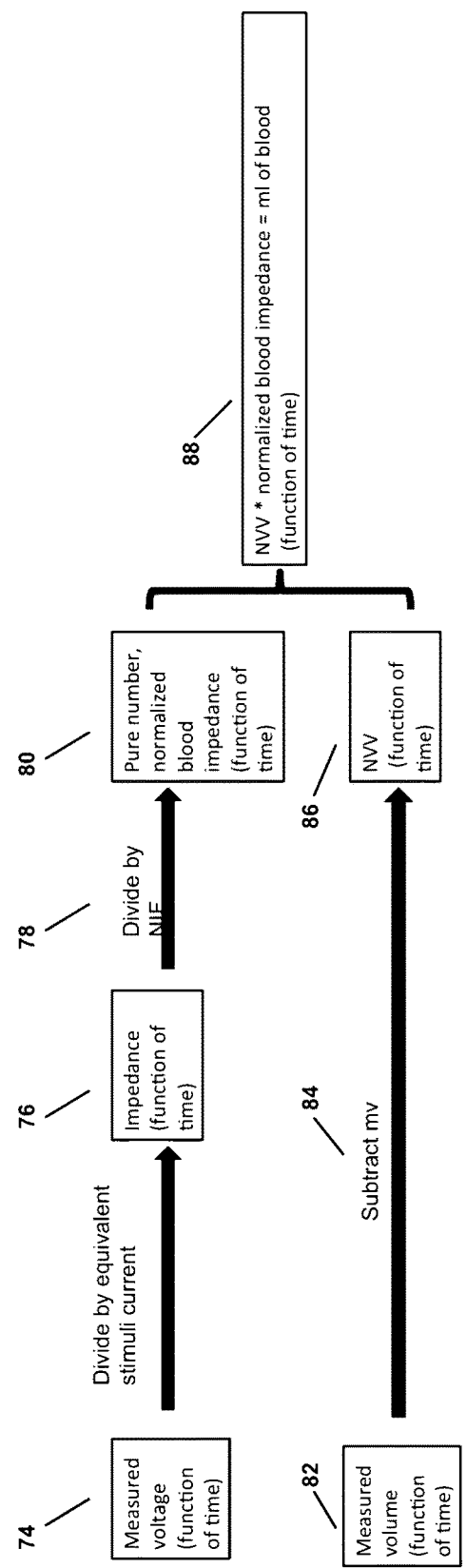
FIG. 9 shows a flow chart of an embodiment for determining blood volume using the monitor of FIG. 1.
Figure 10:
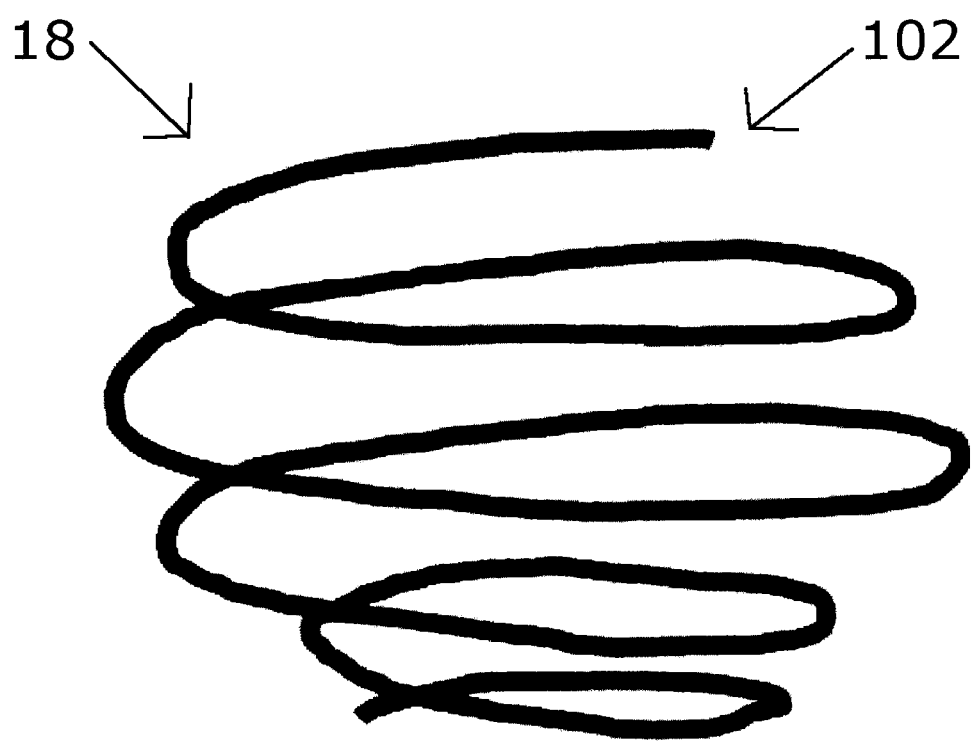
FIG. 10 shows a schematic representation of an embodiment of a volume determining mechanism of the monitor.
Figure 11:
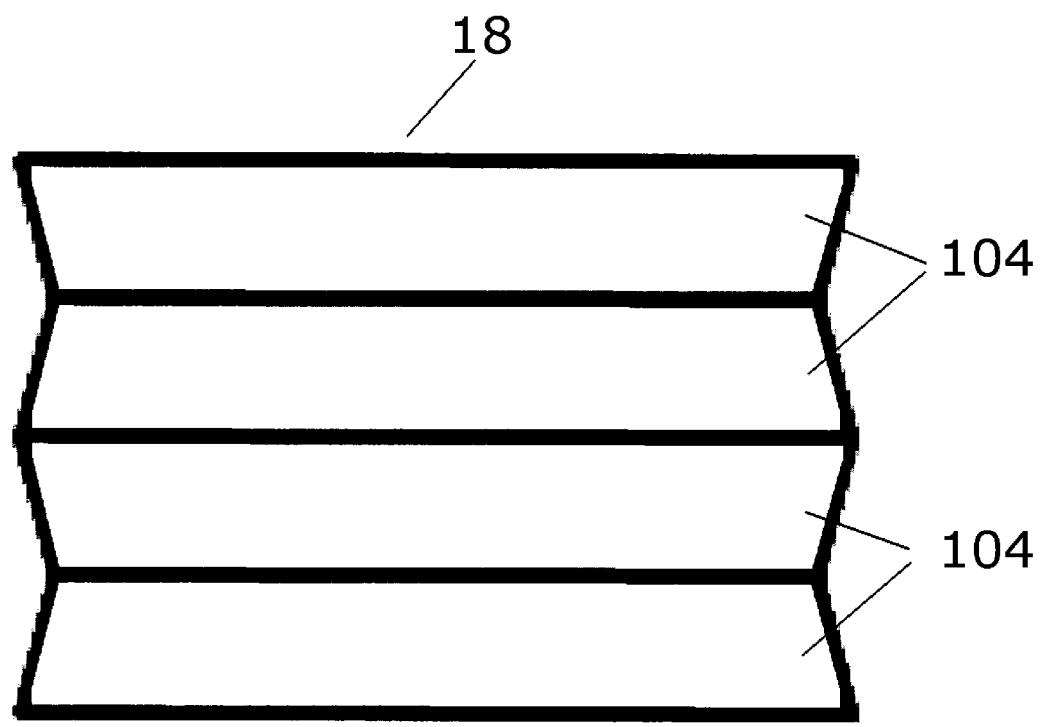
FIG. 11 shows a schematic representation of another embodiment of a volume determining mechanism of the monitor.

Referring to FIG. 9 of the drawings, a schematic flowchart of a computationally simple method of determining blood volume as a function of time is illustrated. The measured voltage of the response signals as shown at 74 is divided by the equivalent stimulus current to provide the time varying impedance as shown at 76. The time varying value of the impedance 76 is then divided by a normalising impedance factor (NIF) 78 to obtain a time varying normalised blood impedance value 80.

The volume determining mechanism 18 determines the time varying volume of the limb 24 of the subject as shown at 82. A minimum value (mv) 84 is subtracted from the measured volume as shown at 84 to obtain a time varying net volume variation (NVV) as shown at 86. The NVV gives a nominal value between 0 and 1 which describes in a computationally simple manner the blood volume in the subject's leg 24. This may be used as a simple method of risk assessment. For example, an NVV of >0.85 may represent high risk, an NVV of <0.5 may represent low risk and somewhere between these two values may represent moderate risk.

Finally, the NVV 86 is multiplied by the normalised blood impedance 80 to obtain a time varying volume of blood in millilitres as shown at 88.

The impedance as measured by any one of the three methods needs to be filtered using a low pass filter at 6 Hz and all artefacts need to be removed. As indicated above, the impedance is then divided by the normalising impedance factor (NIF) recorded during calibration to transform the impedance into a normalised number having a value less than 1.

The normalising impedance factor (NIF) is calculated during calibration by determining the maximum tissue value and the minimum tissue value and obtaining the average of these two values. The maximum tissue value is measured when the subject is in a standing position for a healthy able bodied person who has not got bleeding wounds. The minimum tissue impedance is calculated with the limb of the subject elevated while the subject is at rest with the limb elevated above the subject's heart.

The minimum volume (mv) is measured at calibration as the average minimum volume across 5 seconds while the subject's limb is at rest supported above the subject's heart.

In another, more computationally complex, but more accurate, method, at calibration, the monitor 10 takes measurements, firstly, while the subject is lying down with leg elevated and then, secondly, with the subject standing up. From the first measurements, a minimum measure of limb section volume (Vm) and a maximum measure of electrical impedance (Ve) is obtained. From the second measurements, a maximum measure of limb section volume (Vm) and a minimum measure of electrical impedance (Ve) is obtained.

This provides a simple linear equation of the form y=mx+c to convert impedance to volume as follows (with two calibration points):

$$\text{Volume (ml)}=(\Delta Vm/\Delta Ve)*(\text{Current measure of } Ve)+c$$

where c may be calculated as $Ve_i+(\Delta Vm/\Delta Ve)*Vm_i$.

Further subtraction of Vm (min) from Volume removes the minimal volume of the limb such that when the limb has minimum blood volume the output is 0 ml.

While only two points are required for calibration, multiple points of calibration can be calculated for higher order polynomial fits. Hence, additional points may be added for example by taking measurements while the subject is lying flat. Also, when a person makes a postural transition, blood volume will gradually change. If there is no additional interference, i.e. movement (as detected by the accelerometers 46), transient calibration can be made.

As described, the NVV determined at 86 is the difference between the measured volume 82 and the minimum volume 84 as shown in FIG. 9.

As previously described, the electrodes 16 are dry electrodes. Hence, there is always a possibility of a high contact impedance being present at any pair of sensing electrodes 16. By rotating, or cycling, the stimulation couple, as described above, using the interface 36, the effect of any high contact impedance resulting from a loose fitting electrode 16 can be minimised.

During calibration, the best value for the contact impedance will be assumed for each pair of electrodes 16. The voltage as detected by each measuring couple for each given stimulation can be used for comparative purposes during the recording of the data. Also, rotating the pair of electrodes 16 used for stimulation at a rate faster than the stimulation rate, should yield similar blood impedance results from each measuring couple and this can be used to detect any stimulation couple that is in loose contact with the skin of the subject.

By averaging the impedance detected by all of the measuring couples for all of the possible combinations of stimuli will reduce the effects of any contact impedance imbalance increasing the signal to noise ratio by a factor $\sqrt{N}$, where N=number of couples.

In addition, the stimulator module 38 is configured also to generate sine waves to perform skin impedance measurements.

One of the applications of the monitor 10 is in the treatment of venous leg ulcers (VLUs). The principle causes of VLUs are high venous stasis. By using the monitor 10, a clinician is able to identify periods of time when the subject is at risk and educate the subject on how this is affecting their healing. The monitor 10 can also provide direct and real-time feedback to a subject, alerting them to their risk status. The subject will then be in a position to initiate stasis-reducing counter-measures to improve VLU healing. Such counter-measures may include instructions to elevate the limb, to walk, or to activate neuromuscular electrical stimulation.

A benefit of the monitor 10 is that it does not generally interfere with the wound itself. Characteristically, VLUs are located at the subject's ankle whereas the monitor 10 is mounted just below the knee of the subject.

It will also be appreciated that the monitor 10 could be used for treating other ulcerative conditions such as arterial ulcers, diabetic ulcers and combination ulcers.

The monitor 10 could also be used to assess the condition of the ulcer. Typically the size of the VLU is captured by the clinician at the time of dressing changes. The size of the VLU is input into the monitor 10 at this time. The subject is able to access his or her records and see how time spent walking, with leg elevated, amounts of stimulation, and risk levels have impacted wound healing. The monitor 10 may also predict by when the VLU would be fully healed should current trends and treatment regimens be continued.

Another application of the monitor 10 is its use in measuring swelling of a patient's limb caused by conditions other than VLUs such as lymph oedema. In addition, the monitor 10 is able to apply stimulation, as described above, to the patient's limb to reduce the swelling.

Still other applications of the monitor 10 include its use in syncope and in high resolution EIP.

In the case of syncope, vasoconstriction of blood vessels in healthy individuals prevents too much blood shifting to lower extremities. However, with some individuals having an inadequate vasoactive response, this may not occur and lead to blood deprivation in the brain with subsequent fainting. The monitor 10 of the disclosure is configured to provide alarms to subjects at risk of fainting by monitoring the volume of blood in the lower leg 24 of the subject.

Yet another application of the monitor 10 is its use in subjects suffering from chronic venous insufficiency. Healthy venous return is dependent on competent venous valves. Break down of these valves leads to retrograde venous flow. Increased blood in the limb leads to increased venous pressure. If maintained, the elevated venous pressure can lead to pain, oedema and ulceration.

To test for venous insufficiency, the veins of the lower leg 24 are emptied and the time to refill the limb is monitored. An example of a subject suffering from chronic venous insufficiency is shown at 90 in FIG. 7 of the drawings in comparison with a graph of a subject with normal venous valves as shown at 92 in FIG. 7 of the drawings. The subject remains motionless until blood volume is stable (baseline); on instruction the subject performs five voluntary contractions of the lower limb muscles. The time taken to return to a stable blood volume indicates the health of the venous valves. Return to baseline (also known as refill time) taking more than 11 seconds indicates healthy valves and, conversely, less than 11 seconds indicates venous insufficiency. Typically voluntary calf contractions (dorsiflexion of the ankle) are used to expel blood from the lower limb. Alternatively the monitor 10 itself is used to effect rapid calf compressions through the activation of a leg worn compression cuff (not shown). The calf contractions/compressions are shown at 94 in FIG. 7 of the drawings.

The emptying of the veins of the lower leg 24 of the subject is achieved by seating the subject on a plinth with knees flexed at 90 degrees. The lower leg 24 is emptied by active contraction, of the leg muscles or pneumatic compression of the lower leg 24.

Typically, a filling time of greater than eleven seconds indicates normal venous valves whereas a filling time of less than eleven seconds denotes venous insufficiency.

A still further application of the monitor 10 is in its use for subjects suffering from peripheral arterial disease which is a particularly serious problem for subjects with diabetes. This results in a thickening and loss of elasticity of arterial vessels. The monitor 10 can be used to detect deficits in arterial circulation based on the shape of impedance tracings i.e. by use of EIP.

As indicated above, the monitor 10 can also be used in the detection of deep vein thrombosis (DVT) or obstructed haemodynamics. Certain subjects have a high risk of developing DVT following general surgery, particularly hip or knee surgery. EIP has been shown to have a high degree of accuracy for detecting DVT when compared to strain gauge and invasive venography.

The monitor 10 together with the cuff 48 (FIG. 3) can be used for detecting DVT or obstructed haemodynamics in the subject. Assessment is performed by placing the cuff 48 around the thigh of the subject and inflating the cuff to 30-40 mmHg, preventing venous return but allowing arterial inflow. The venous constriction causes pooling in the limb observed via EIP as a reduction in impedance. When the blood volume during occlusion plateaus maximum venous capacity is achieved.

The cuff 48 is then rapidly deflated and the decreasing impedance during the first 3 seconds of the cuff deflation is monitored. The decrease in impedance for a normal individual is shown as trace 96 in FIG. 8 of the drawings whereas a subject suspected of having DVT has a trace as shown at 98 in FIG. 8 of the drawings.

For subjects with VLU, the monitor 10 can be used as a stimulator for effecting neuromuscular electrical stimulation as shown in FIG. 4 of the drawings. Neuromuscular electrical stimulation has been shown to create a major improvement in VLU subjects, in particular, subjects at rest. Bed rest causes a significant reduction in venous blood flow after approximately 4 hours. However, with neuromuscular electrical stimulation, venous blood flow at rest can be maintained at substantially normal rates.

A benefit of this application of the monitor 10 is that it can be used with orthopaedic implants and provides painless neuromuscular electrical stimulation.

The monitor makes use of stimulating electrodes 50 (FIG. 4) and includes a control device 100 which is able to be used by the subject to control stimulation either by means of a preprogramed control device 100 or by the subject manually operating the control device 100.

An advantage of using the monitor 10 to effect neuromuscular electrical stimulation is that it targets calf muscle pump function, minimal clinic supervision is required, it is portable, wearable and silent and has high compliance with medical safeguards.

The monitor 10 is able to signal to an able bodied subject when neuromuscular electrical stimulation should be effected or, in the case of a non-able bodied subject, automatically starts stimulating muscle with intent to generate muscle contractions.

Figure 12:
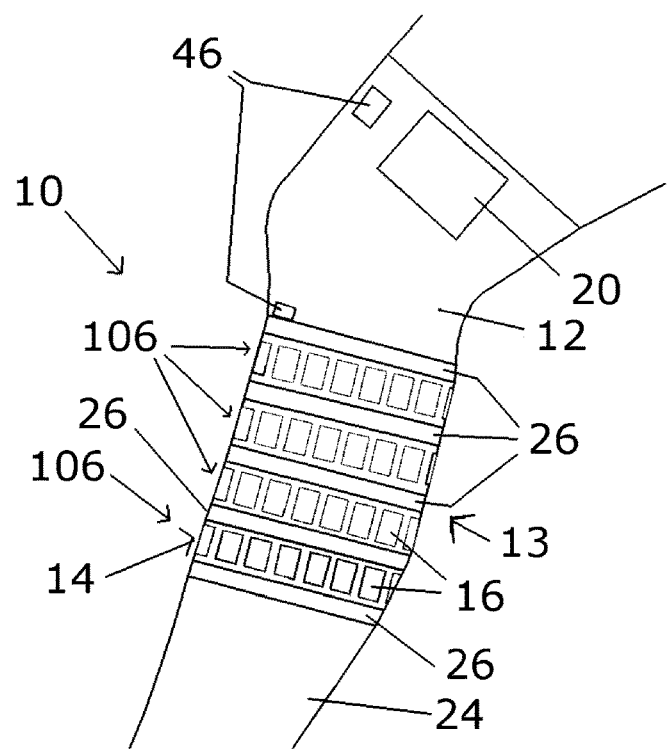
FIG. 12 shows a schematic representation of a further embodiment of the blood volume monitor.

FIG. 12 shows an embodiment of the blood volume monitor used for high resolution EIP. With reference to previous embodiments, like reference numerals refer to like parts unless otherwise specified.

In this embodiment, the sensing arrangement 14 of the monitor 10 comprises a high density configuration of electrodes 16. As illustrated, the electrodes 16 are smaller and are arranged in a plurality of spaced, stacked rings 106. Each ring 106 of electrodes 16 is separated by a band 26 of the volume determining mechanism 18 of the monitor 10. This arrangement increases the number of electrodes 16 about the circumference of the sleeve 12 and along the limb of interest. The increased density of electrodes 16 about the limb as well as the increased accuracy of volume measurement as provided by the increased number of bands 26 facilitates three-dimensional realisation of limb haemodynamics, effectively in real-time. The monitor 10 therefore provides a viable, non-invasive method for isolation of thrombi among other applications and provides for DVT localisation without the associated high costs, invasiveness and side effects of existing techniques.

The spaced rings 106 of electrodes 16 can also be used to detect the transition of a blood pulse at multiple points along the patient's limb so as to measure pulse transition time. As the distance between each ring 106 is known, this is able to be used to calculate pulse wave velocity which is a useful measure of arterial stiffness.

This can also be achieved by use of the bands 26 which, being electro-resistive, can be employed for measuring purposes to detect passage of the blood pulse.

Still further, both the rings 106 of electrodes 16 and spaced electro-resistive bands 26 can be used to detect the transition of a blood pulse at multiple points along the patient's body so as to measure a transit time of the pulse. As the distance between each ring 106 or band 26, as the case may be, is known this can also be used to calculate pulse wave velocity. Pulse wave velocity is a very useful measure of arteriosclerosis in peripheral limbs of the subject.

Where an ECG signal, or other suitable cardiac signal is available, pulse wave transit time and pulse wave velocity may be derived for the distance between the patient's heart and the monitor 10. It may also be used to estimate central blood pressure.

As the pulse wave velocity and the pulse volume are both measurable, blood pressure changes are able to be derived using a Bramwell-Hills equation, or others.

Figure 13:
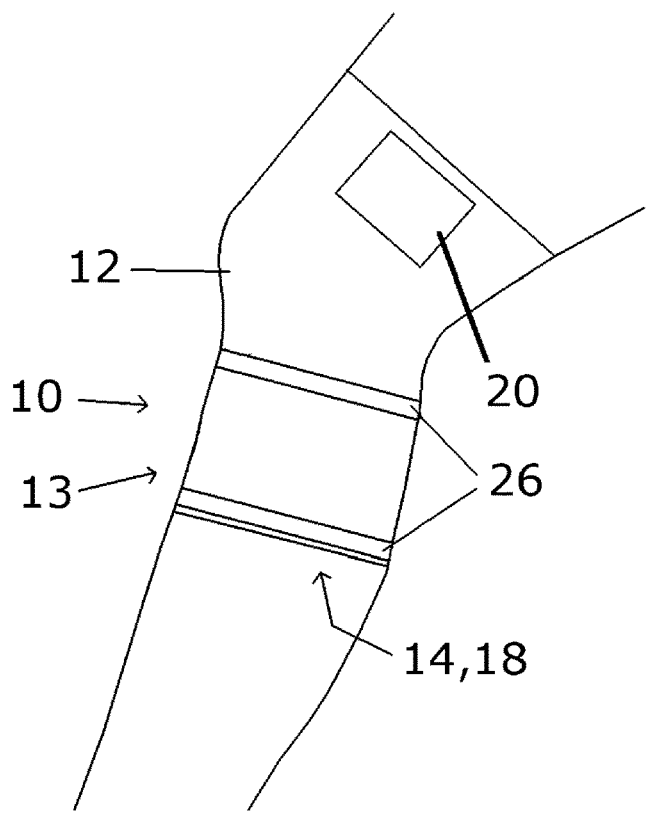
FIG. 13 shows a schematic representation of still a further embodiment of the blood volume monitor.

With reference to FIG. 13 of the drawings, a further implementation of the monitor 10 is illustrated. With reference to the previous drawings, like reference numerals refer to like parts, unless otherwise specified.

In this embodiment, the measuring arrangement 13 of the monitor 10 comprises only the volume determining mechanism 18 which functions to measuring both the volume of the part of the limb, such as the subject's lower leg 24, and the blood volume. The bands 26 are, as described above, resiliently flexible and their resistance changes with extension and contraction of the bands and can therefore additionally serve as the sensing arrangement 14.

As blood flows beneath the carrier 12, slight extensions and contractions of the bands 26 occur. The signal conditioning module 44 of the control unit 20 is sufficiently sensitive to detect these slight extensions and contractions of the bands 26. Thus, the bands 26 are able to measure both the volume of the part of the subject's limb and variations in the dimensions of the bands 26 measure blood volume change. From these measurements, blood volume in millilitres is able to be calculated. While the embodiment of FIG. 13 shows that the measuring arrangement 13 uses the spaced bands 26, in another embodiments the components 102 and 104 of FIGS. 10 and 11 of the drawings, respectively, could be used as the measuring arrangement 13 for both volume determination and sensing.

Figure 14:
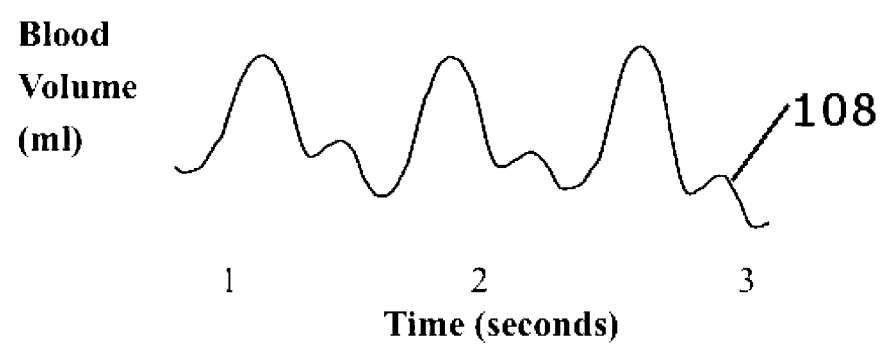
FIG. 14 shows a graphical representation of processed data output from the blood flow monitor of at least FIG. 2 of the drawings.

An advantage of the monitor 10 is that it enables blood volume change to be captured and displayed. As the electrical impedance mechanism is calibrated to volume, the impedance change during transit of the pulse wave is able to be captured and displayed, that impedance change being representative as a blood volume change. From this information, the entire pulse volume is able to be calculated as well as systolic and diastolic portions as shown in FIG. 14 of the drawings.

The monitor 10 of the present disclosure has numerous additional advantages. These include self-calibration. As indicated above, comparison of physical volume and EIP in static unchanging positions allows for the collection of calibration points. Calibration points may also be determined during changes in limb volume when movement is not detected. As a result, calibration may be achieved in clinical test scenarios, for example, during venous occlusion, or "on-the-fly" during periods when the subject is motionless, as detected via the accelerometers 46.

The monitor 10 has the convenience that it is wearable and light and requires no or minimal training to give useful, reproducible results. The monitor 10 is designed to be donned and removed easily. It is able to be positioned at any of a number of sites on any limb of interest. No skin preparation is required due to the high input impedance of the device nor is extensive training required for use. Also, there is no need to use contact gels are other conductivity enhancing materials for the electrodes. As will be appreciated, the efficacy of conductive gels degrades over time precluding their use for extended periods of time.

A related advantage is that the monitor can be set up in as matter of seconds in comparison with the 10 to 15 minutes required with existing EIP systems.

Because the monitor 10 is capable of coping with high common-mode noise artefacts and a small differential signal, a high concentration of sensing electrodes could be used resulting in substantially higher resolution of the underlying haemodynamics.

Also, because the monitor 10 is able to be worn without discomfort, haemodynamics can be monitored over the long-term. Combined with accelerometers 46 in the monitor 10, this enables non-intrusive long-term monitoring of peripheral haemodynamics and the ability to relate this information directly to posture, changes in posture, activity patterns and exercise. Also, as indicated above, the monitor 10 can be used as a stimulator for effecting muscle and related EMG activity monitoring.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A blood volume monitor comprising:
a carrier mountable about a part of a body of a subject, the carrier comprising a sleeve of a resiliently flexible material;
at least two bands carried by the sleeve and circumscribing two parts of the part of the body underlying the sleeve, wherein the at least two bands comprise an electrically resistive material configured to expand and contract in unison with the sleeve, wherein the at least two bands are in fixed positions relative to each other on the sleeve with a known distance between the at least two bands and configured to approximate a truncated cone, wherein the at least two bands are configured to provide output resistivity response signals representative of the volume of the part of the body of the subject underlying the sleeve and circumscribed by the at least two bands and wherein a change in volume of the part of the body of the subject underlying the sleeve is determined by a difference in volume at two time points determined from the output resistivity response signals representative of the volume, and wherein the at least two bands are calibrated to provide volume estimation within a specified tolerance of specific calibration values; and
a controller in communication with the at least two bands, the controller being configured to process data output by the at least two bands to determine, using the volume data provided by the at least two bands and change in resistivity of the at least two bands, the volume of the part of the body of the subject underlying the sleeve and to determine a change in blood volume in the part of the body of the subject, the controller configured to use the output resistivity response signals received from the at least two bands and the determined volume of the part of the body to determine the change in blood volume, wherein the controller contains the specific calibration values as parameters to perform volume measurements.

2. The monitor of claim 1, wherein the output resistivity response signals represent a blood impedance value of blood in the part of the body of the subject.

3. The monitor of claim 1, further comprising a plurality of sets of sensors attached to the sleeve and configured to measure changes in impedance in the part of the body of the subject, such changes in impedance being indicative of blood volume changes in the part of the body of the subject, one set of the sensors operating at any one time as stimulators configured to stimulate the part of the body of the subject with at least one of the other sets of sensors sensing response signals evoked in the part of the body of the subject.

4. The monitor of claim 3, wherein each sensor of the plurality of sets of sensors is an electrode, the electrodes being arranged at circumferentially spaced intervals about the sleeve and each set of electrodes comprising a pair of opposed electrodes.

5. The monitor of claim 4, wherein one of the pairs of electrodes is configured to be used at any one time as stimulating electrodes and at least one other pair of electrodes, rotated about the carrier relative to the one pair of electrodes, is used as sensing electrodes.

6. The monitor of claim 5, wherein the controller is operable to cycle through the pairs of electrodes periodically to vary which pair of electrodes is operating as the stimulating electrodes and which pair of electrodes is being used as sensing electrodes.

7. The monitor of claim 6, wherein the controller is operable to cycle through the sets of electrodes to select the stimulating set of electrodes prior to the stimulating set of electrodes stimulating underlying tissue of the subject.

8. The monitor of claim 3, wherein a stimulating signal output by the stimulating set of sensors is one of a sine wave signal and a uniform pulse waveform.

9. The monitor of claim 8, wherein an amplitude of the stimulating signal is selected to be lower than a level at which the subject is aware of the stimulation.

10. The monitor of claim 9, wherein the controller is operable to vary the amplitude of the stimulating signal to account for changes in at least one of contact impedance and muscle contraction/relaxation.

11. The monitor of claim 1, which is configured to impart muscular stimulation to muscles of the subject.

12. The monitor of claim 1, wherein an array is configured to provide both volume data and measure change in volume of the part of the body of the subject underlying the carrier to output the response signals representative of the change in volume.

13. The monitor of claim 1, comprising a position detector configured to detect a position of the part of the body of the subject.

14. The monitor of claim 1, comprising a pressure applicator, configured to impart pressure to the part of the body of the subject.

15. A method of monitoring blood volume in a subject, the method comprising:
mounting a blood volume monitor to a body part of the subject, wherein the blood volume monitor comprises:
a carrier mountable about the body part of the subject, the carrier comprising a sleeve of a resiliently flexible material;
at least two bands carried by the sleeve and circumscribing two parts of the part of the body underlying the sleeve, wherein the at least two bands comprise an electrically resistive material configured to expand and contract in unison with the sleeve, wherein the at least two bands are in fixed positions relative to each other on the sleeve with a known distance between the at least two bands and configured to approximate a truncated cone, wherein the at least two bands are configured to provide output resistivity response signals representative of the volume of the body part of the subject underlying the sleeve and circumscribed by the at least two bands and wherein a change in volume of the body part of the subject underlying the sleeve is determined by a difference in volume at two time points determined from the output resistivity response signals representative of the volume, and wherein the at least two bands are calibrated to provide volume estimation within a specified tolerance of specific calibration values; and
a controller in communication with the at least two bands, the controller being configured to process data output by the at least two bands to determine, using the volume data provided by the at least two bands and change in resistivity of the at least two bands, the volume of the body part of the subject underlying the sleeve and to determine a change in blood volume in the body part of the subject, the controller configured to use the output resistivity response signals received from the at least two bands and the determined volume of the body part of the subject to determine the change in blood volume, wherein the controller contains the specific calibration values as parameters to perform volume measurements;
determining an initial volume of the body part of the subject using volume data provided by the at least two bands that define the truncated cone;
outputting response signals representative of a change in volume of the body part of the subject; and
using the response signals to determine a change in volume of blood in the body part of the subject based on the initial volume of the body part of the subject, the sensed change in volume of the body part of the subject and the specific calibration values.

16. The method of claim 15, wherein the monitor further comprises a plurality of sets of sensors attached to the sleeve and configured to measure changes in impedance in the body part of the subject, such changes in impedance being indicative of blood volume changes in the body part of the subject, a first set of the sensors operating at any one time as stimulators configured to stimulate the body part of the subject and at least a second set of sensors sensing response signals evoked in the body part of the subject, wherein the method comprises sensing the change in volume in the body part of the subject by sensing a change in impedance of blood within the body part of the subject.

17. The method of claim 16, comprising sensing the changes in impedance by stimulating the body part of the subject with the first set of sensors and monitoring the evoked response with the second set of sensors.

18. The method of claim 17, comprising cycling through the sets of sensors to vary which set of sensors is functioning as the set of stimulating sensors at any one time.

19. The method of claim 17, comprising effecting stimulation of the body part of the subject with a stimulating signal comprising one of a sine wave signal and a uniform pulse waveform.

20. The method of claim 19, comprising selecting an amplitude of the stimulating signal to be lower than a level at which the subject is aware of the stimulation.

21. The method of claim 20, comprising varying the amplitude of the stimulating signal to account for changes in contact impedance or muscle contraction/relaxation.

22. The method of claim 15, comprising imparting muscular stimulation to muscles of the subject.

23. The method of claim 15, comprising detecting a position of the body part of the subject.

24. The method of claim 15, comprising imparting pressure to the body part of the subject.

25. The method of claim 15, wherein the volume of the body part of the subject is calculated according to the following formula:

$$V=(\pi/3)(h)(b^2+ab+a^2),$$

wherein:
a and b are radii of two of the at least two bands calculated from the output resistivity response signals, and
h is a height of the truncated cone between the two of the at least two bands.

* * * * *